US009802885B2

(12) United States Patent
Lombardo et al.

(10) Patent No.: US 9,802,885 B2
(45) Date of Patent: Oct. 31, 2017

(54) SUBSTITUTED CYCLOHEXANE COMPOUNDS

(75) Inventors: Louis J. Lombardo, Washingtonville, NY (US); Michael E. Lankin, High Bridge, NJ (US); Jaime M. Ferreira, Park Ridge, NJ (US); Jennifer B. Tartaglia, Midland Park, NJ (US); John D. Zanone, Towaco, NJ (US); Amrit Mankoo, Middletown, NY (US)

(73) Assignee: TAKASAGO INTERNATIONAL CORPORATION (USA), Rockleigh, NJ (US)

( * ) Notice: Subject to any disclaimer, the term of this patent is extended or adjusted under 35 U.S.C. 154(b) by 800 days.

(21) Appl. No.: 14/131,920

(22) PCT Filed: Aug. 31, 2012

(86) PCT No.: PCT/US2012/053290
§ 371 (c)(1),
(2), (4) Date: Aug. 19, 2014

(87) PCT Pub. No.: WO2013/033501
PCT Pub. Date: Mar. 7, 2013

(65) Prior Publication Data
US 2015/0030744 A1    Jan. 29, 2015

Related U.S. Application Data

(60) Provisional application No. 61/530,222, filed on Sep. 1, 2011.

(51) Int. Cl.
| | |
|---|---|
| C07C 233/60 | (2006.01) |
| A23L 1/226 | (2006.01) |
| C07C 69/67 | (2006.01) |
| C07C 69/675 | (2006.01) |
| C07C 59/62 | (2006.01) |
| C07C 233/10 | (2006.01) |
| C07C 233/58 | (2006.01) |
| C07C 69/708 | (2006.01) |
| A23L 27/20 | (2016.01) |

(52) U.S. Cl.
CPC .......... *C07C 233/60* (2013.01); *A23L 27/203* (2016.08); *A23L 27/204* (2016.08); *A23L 27/205* (2016.08); *C07C 59/62* (2013.01); *C07C 69/67* (2013.01); *C07C 69/675* (2013.01); *C07C 69/708* (2013.01); *C07C 233/10* (2013.01); *C07C 233/58* (2013.01); *C07C 2601/14* (2017.05)

(58) Field of Classification Search
CPC ... C07C 233/60; C07C 233/58; C07C 233/10; C07C 59/62; C07C 69/67; C07C 69/675; C07C 2601/14; A23L 27/203; A23L 27/204; A23L 27/205
See application file for complete search history.

(56) References Cited

U.S. PATENT DOCUMENTS

| | | | |
|---|---|---|---|
| 4,150,052 | A | 4/1979 | Watson et al. |
| 4,459,425 | A | 7/1984 | Amano et al. |
| 5,773,410 | A | 6/1998 | Yamamoto |
| 6,328,982 | B1 | 12/2001 | Shiroyama et al. |
| 6,673,844 | B2 | 1/2004 | Kumamoto et al. |
| 6,780,443 | B1 | 8/2004 | Nakatsu et al. |
| 6,838,106 | B2 | 1/2005 | Kumamoto et al. |
| 6,884,906 | B2 | 4/2005 | Dewis et al. |
| 6,890,567 | B2 | 5/2005 | Nakatsu et al. |
| 6,899,901 | B2 | 5/2005 | Nakatsu et al. |
| 6,956,139 | B2 | 10/2005 | Green et al. |
| 2008/0096969 | A1 | 4/2008 | Ley |
| 2009/0123355 | A1 | 5/2009 | Chander et al. |
| 2010/0076080 | A1 | 3/2010 | Yelm et al. |
| 2010/0234260 | A1 | 9/2010 | Sekine et al. |
| 2012/0165559 | A1 | 6/2012 | Mane et al. |

FOREIGN PATENT DOCUMENTS

| | | |
|---|---|---|
| DE | 2 115 130 | 10/1972 |
| WO | WO 00/62737 A1 | 10/2000 |
| WO | WO 2005/023749 | 3/2005 |
| WO | WO 2005/049553 | 6/2005 |
| WO | WO 2005/097735 | 10/2005 |
| WO | WO 2005/115325 | 12/2005 |
| WO | WO 2007/100450 | 9/2007 |
| WO | WO 2009/123355 | 10/2009 |
| WO | WO 2010/019730 | 2/2010 |
| WO | WO 2010/122239 A1 | 10/2010 |

OTHER PUBLICATIONS

Rykowski, Z., Gubrynowicz, O. 1993. "Reaction of (+) Dihydroxycarveol Tosylate with KCN in Apriotic Solvents (-)(1S,2R,4S) 1-Methyl-4-isopropenylcyclohexane-2-carbonitrile." Annales Universitatie Mariae Curie-Sklowdowsk Lublin-Polonia. vols. 48-49, pp. 137-147.*
Jefford, C.W., Wang, Y., Bernardinelli, G. 1988. "Mechanistic and Synthetic Studies on the Formation of 1,2,4-Trioxanes Related to Arteannuin. Photooxygenation of a Bicyclic Dihydropyran." Helvetica Chimica Acta. vol. 71, pp. 2042-2052.*
deBoer, J.J.J., Speckamp, W.N. 1975. "ω-Carbinollactams in regioselective olefinsynthesis." Tetrahedron Letters. vol. 46, pp. 4039-4042.*
Andersen Niels H. et al, "Acetyl cation facilitated cyclizations of olefinic aldehydes. III. Factors determining regiochemistry in acroleins", *Synthetic Communications: An International Journal for Rapid Communication of Synthetic Organic Chemistry*, Taylor & Francis Inc., Philadelphia, PA; US, vol. 8, No. 7, Jan. 1, 1978 (Jan. 1, 1978), pp. 437-448.
Erman et al., "New developments in physiological cooling agents", *Perfumer & Flavorist*, Allured Publishing Corp., vol. 32, Jan. 1, 2007 (Jan. 1, 2007), p. 20.

(Continued)

*Primary Examiner* — Nikki H Dees
(74) *Attorney, Agent, or Firm* — Baker Botts L.L.P.

(57) ABSTRACT

The presently disclosed subject matter is directed to novel compounds of Formula I, Formula II, and Formula III, and stereoisomers thereof, and flavor compositions comprising the novel compounds.

14 Claims, No Drawings

(56) References Cited

OTHER PUBLICATIONS

Jefford C. W. et al., "215. Mechanistic and Synthetic Studies on the Formation of 1,2,4-Trioxanes related to Arteannuin. Photooxygenation of a bicyclic Dihydropyran", *Helvetica Chimica Acta*, vol. 71, 1988, pp. 2042-2052.
Supplemental European Search Report mailed Nov. 12, 2015 in EP Application No. 12827781.
Dean et al., "Citronellel cyclisation in superacids", J. Chem, Soc. Perkin Trans., 2:1275-1277 (1990).
Furrer et al., "New developments in the chemistry of cooling compounds", *Chemosensory Perception*, 1(2):119-126 (2008).
Watson et al., "New compounds with the menthol cooling effect", *J. Soc. Cosmet. Chem*, 29:185-200 (1978).

\* cited by examiner

SUBSTITUTED CYCLOHEXANE COMPOUNDS

CROSS-REFERENCE TO RELATED APPLICATIONS

The present application is a National Phase Application of International Patent Application No. PCT/US2012/053290 filed Aug. 31, 2012, which claims priority to U.S. Provisional Application Ser. No. 61/530,222, filed Sep. 1, 2011, the contents of which are is hereby incorporated by reference in their entireties and to each of which priority is claimed.

FIELD OF THE INVENTION

The presently disclosed subject matter is directed to novel compounds of Formulas I, II, and III, and stereoisomers thereof. In addition, the presently disclosed subject matter is directed to flavor compositions comprising the novel compounds.

BACKGROUND OF THE INVENTION

The presently disclosed subject matter discloses a series of novel compounds derived from 5-methyl-2-(prop-1-en-2-yl)cyclohexanol, commonly known as isopulegol, as shown below.

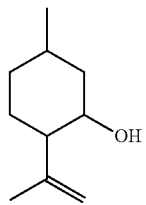

Isopulegol has been used in various consumer products across the flavor and fragrance industry. See U.S. Pat. Nos. 5,773,410 and 6,328,982; U.S. Publication No. 2010/0234260; and Japanese Patent No. JP 6065023.

Specific derivatives of isopulegol, which have incorporated the backbone of 1-methyl-4-isopropenylcyclohexane, are known to possess various sensory attributes. For example, International Patent Publication No. WO 2009/123355 discloses a number of compounds providing a prolonged cooling effect, including various isopulegyl carbonates. International Patent Publication No. WO 2005/023749 discloses various isopulegyl carbonates and methods for producing thereof. International Patent Publication No. WO 2005/115325 discloses both menthyl and isopulegyl polyethers, which provide a cooling effect. German Patent No. DE 2115130 discloses various aliphatic and aromatic isopulegyl esters and uses in fragrance applications thereof. U.S. Patent Publication No. 2012/0165559 discloses compounds having physiological effects, particularly a cooling or warming on the skin or mucous membranes. Additionally, examples of derivatives of 5-methyl-2-isopropyl-cyclohexanol, commonly known as menthol, have been disclosed with varying sensory attributes. See Watson et al., *J. Soc. Cosmet. Chem.* (1978); 29:185-200; Furrer et al., *Chem. Percept.* (2008); 1:119-126; U.S. Pat. Nos. 4,150,052; 4,459,425; 6,884,906; and International Patent Publication Nos.: WO 2005/049553; WO 2005/097735; WO 2007/100450; and WO 2010/019730.

It is recognized that combinations of materials (e.g., cooling agent, warming agent, and/or tingling agents) that impart sensory effects to the skin of a subject, such as the oral or nasal cavity or other topical areas, are known in the art. For example, U.S. Pat. No. 6,328,982 discloses cool feeling compositions comprising a cooling ingredient and a warming ingredient, e.g., vanillyl butyl ether. U.S. Pat. Nos. 6,780,443, 6,890,567, and 6,899,901 disclose compositions comprising a warming ingredient, a cooling ingredient, and a tingling ingredient. U.S. Pat. Nos. 6,673,844 and 6,838,106 disclose warming compositions comprising a cooling ingredient and a particular compound.

There remains a substantial interest and a need in the art for new preparations of novel flavor and fragrance components with favorable organoleptic and sensory properties. The presently disclosed subject matter provides a pathway for the development of such compounds derived from isopulegol having desirable sensory properties by inducing various chemical reactions at the hydroxyl functionality.

SUMMARY OF THE INVENTION

The presently disclosed subject matter provides novel compounds of Formula I, II, and III, or stereoisomers thereof. The presently disclosed subject matter also discloses flavor compositions comprising these compounds.

In one embodiment, the presently disclosed subject matter provides a compound of Formula I or a stereoisomer thereof,

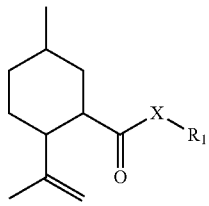

Formula I wherein X is O or N—$R_2$, and wherein $R_1$ and $R_2$ are selected from the group consisting of H, alkyl groups, alkenyl groups, aryl groups, and heteroaryl groups. In some embodiments, each of H, the alkyl groups, the alkenyl groups, the aryl groups, and the heteroaryl groups is substituted with at least one selected from the group consisting of hydroxy groups, alkoxy groups, carboxy groups, carboalkoxy groups, carboxamide groups, and nitrile groups. In certain embodiments, the compound is selected from the group consisting of N-ethyl-5-methyl-2-(prop-1-en-2-yl)cyclohexanecarboxamide, N-cyclopropyl-5-methyl-2-(prop-1-en-2-yl)cyclohexanecarboxamide, N-isopropyl-5-methyl-2-(prop-1-en-2-yl)cyclohexanecarboxamide, N-(tert-butyl)-5-methyl-2-(prop-1-en-2-yl)cyclohexanecarboxamide, N-(sec-butyl)-5-methyl-2-(prop-1-en-2-yl)cyclohexanecarboxamide, ethyl 2-(5-methyl-2-(prop-1-en-2-yl)cyclohexanecarboxamido)acetate, N-(4-methoxyphenyl)-5-methyl-2-(prop-1-en-2-yl)cyclohexanecarboxamide, and N-(4-(cyanomethyl)phenyl)-5-methyl-2-(prop-1-en-2-yl)cyclohexanecarboxamide. In one specific embodiment, the compound is N-ethyl-5-methyl-2-(prop-1-en-2-yl)cyclohexanecarboxamide. In another embodiment, the compound is N-(4-(cyanomethyl)phenyl)-5-methyl-2-(prop-1-en-2-yl)cyclohexanecarboxamide.

In another embodiment, the presently disclosed subject matter provides a compound of Formula II or a stereoisomer thereof,

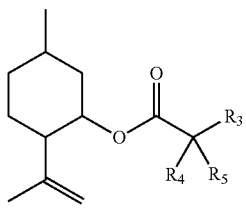

Formula II wherein $R_3$, $R_4$, and $R_5$ are selected from the group consisting of H, alkyl groups, alkenyl groups, aryl groups, and heteroaryl groups, and wherein $R_5$ is not H, a $C_1$-$C_{10}$ aliphatic group, or a $C_1$-$C_{10}$ aromatic group when both $R_3$ and $R_4$ are H. In some embodiments, each of H, the alkyl groups, the alkenyl groups, the aryl groups, and the heteroaryl groups is substituted with at least one selected from the group consisting of hydroxy groups, alkoxy groups, carboxy groups, carboalkoxy groups, carboxamide groups, and nitrile groups. In certain embodiments, the compound is selected from the group consisting of 4-((5-methyl-2-(prop-1-en-2-yl)cyclohexyl)oxy)-4-oxobutanoic acid, 5-((5-methyl-2-(prop-1-en-2-yl)cyclohexyl)oxy)-5-oxopentanoic acid, 5-methyl-2-(prop-1-en-2-yl)cyclohexyl 2-hydroxypropanoate, 5-methyl-2-(prop-1-en-2-yl)cyclohexyl 3-oxobutanoate, and 5-methyl-2-(prop-1-en-2-yl)cyclohexyl 3-hydroxybutanoate.

In one embodiment, the presently disclosed subject matter provides a compound of Formula III or a stereoisomer thereof,

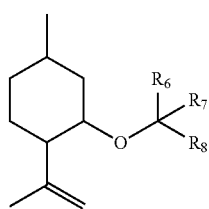

Formula III wherein $R_6$, $R_7$, and $R_8$ are selected from the group consisting of H, alkyl groups, alkenyl groups, aryl groups, and heteroaryl groups, and wherein $R_8$ is not a polyether when both $R_6$ and $R_7$ are H. In some embodiments, each of H, the alkyl groups, the alkenyl groups, the aryl groups, and the heteroaryl groups is substituted with at least one selected from the group consisting of hydroxy groups, alkoxy groups, carboxy groups, carboalkoxy groups, carboxamide groups, and nitrile groups. In certain embodiments, the compound is selected from the group consisting of 2-((5-methyl-2-(prop-1-en-2-yl)cyclohexyl)oxy)acetic acid, and N-isobutyl-2-((5-methyl-2-(prop-1-en-2-yl)cyclohexyl)oxy)acetamide.

In one embodiment, the presently disclosed subject matter provides a flavor composition comprising from about 0.0001% to about 99% of Formula I or a stereoisomer thereof. In one embodiment, the presently disclosed subject matter provides a flavor composition comprising from about 0.0001% to about 99% of Formula II or a stereoisomer thereof. In one embodiment, the presently disclosed subject matter provides a flavor composition comprising from about 0.0001% to about 99% of Formula III or a stereoisomer thereof, In one embodiment, the compound of Formula I, II, or III, is present in an amount from about 0.001% to about 50% weight by weight in a flavor composition. In another embodiment, the compound of Formula I, II, or III, is present in an amount from about 0.01% to about 20% weight by weight in a flavor composition. In one embodiment, the flavor composition further comprises at least one sensation invoking material. In certain embodiments, the sensation invoking material is selected from the group consisting of a warming ingredient, a cooling ingredient, a tingling-type ingredient, and a combination thereof.

DETAILED DESCRIPTION OF THE INVENTION

The presently disclosed subject matter provides novel compounds of Formula I, II, and III, and stereoisomers thereof. The presently disclosed subject matter also discloses flavor compositions comprising these compounds.

A. Definitions

The examples provided in the definitions present in the present application are non-inclusive unless otherwise stated. They include but are not limited to the recited examples.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the presently disclosed subject matter and includes geometric isomers. It is understood that a substituent may be attached at a chiral center of a carbon atom. Therefore, the presently disclosed subject matter includes enantiomers, diastereomers or racemates of the compound. As used herein, the term "enantiomers" refers to a pair of stereoisomers that are non-superimposable mirror images of each other. A 1:1 mixture of a pair of enantiomers is a "racemic" mixture. The term is used to designate a racemic mixture where appropriate. As used herein, the term "diastereoisomers" refers to stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. The compounds of the presently disclosed subject matter contain one or more asymmetric centers and may thus give rise to enantiomers, diastereomers, and other stereoisomeric forms that may be defined, in terms of absolute stereochemistry, as (R)- or (S)-. The presently disclosed subject matter is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, "alkyl" or "alkyl group" includes both branched, cyclic, and straight-chain saturated aliphatic hydrocarbon groups having the specified number of carbon atoms. $C_{1-6}$ alkyl, for example, includes $C_1$, $C_2$, $C_3$, $C_4$, $C_5$, and $C_6$ alkyl groups. Examples of alkyl include, but are not limited to, methyl, ethyl, n-propyl, isopropyl, n-butyl, isobutyl, sec-butyl, t-butyl, n-pentyl, sec-pentyl, 3-(2-methyl)butyl, 2-pentyl, 2-methylbutyl, neopentyl, n-hexyl, 2-hexyl, and 2-methylpentyl.

As used herein, "alkenyl" or "alkenyl group" refers to an unsaturated branched, straight-chain or cyclic monovalent hydrocarbon radical having at least one carbon-carbon double bond derived by the removal of one hydrogen atom from a single carbon atom of a parent alkene. The radical may be in either the cis or trans conformation about the double bond(s). Examples of alkenyl include, but are not limited to, ethenyl, propenyls, such as prop-1-en-1-yl, prop-1-en-2-yl, prop-2-en-1-yl, prop-2en-2-yl, cycloprop-1-en-1-yl; cycloprop-2-en-1-yl; butenyls such as but-1-en-1-yl, but-1-en-2-yl, 2-methyl-prop-1-en-1yl, but-2-en-1-yl, but-2-en-1-yl, but-2-en-2-yl, buta-1,3-dienl-yl, beta-1,3-dien-2-yl, cyclobut-1-en-1-yl, cyclobut-1-en3-yl, cyclobuta-1,3-dien-1-yl.

As used herein, "aryl" or "aryl group" refers to any stable 6, 7, 8, 9, 10, 11, 12, 13, or 14 membered monocyclic, bicyclic, or tricyclic ring, wherein at least one ring, if more than one is present, is aromatic. Examples of aryl include, but are not limited to, fluorenyl, phenyl, naphthyl, thienyl, indolyl, indanyl, adamantyl, phenantrenyl, and tetrahydronaphthyl.

As used herein, an "alkynyl" or "alkynyl group" refers to an unsaturated branched, straight-chain or cyclic monovalent hydrocarbon radical having at least one carbon-carbon triple bond derived by the removal of one hydrogen atom from a single carbon atom of a parent alkyne. Examples of alkynyl groups include, but are not limited to, ethynyl, propynyl, butynyls, propargyl, and the like.

As used herein, the term "aliphatic" encompasses alkyl, alkenyl and alkynyl, which are defined above.

As used herein, a "carboxy" or "carboxy group" refer to a —COOH group.

As used herein, a "carboalkoxy" or "carboalkoxy group" refers to a —COO-alkyl group, where "alkyl" is defined above.

As used herein, a "carboxamide" or "carboxamide group" refers to a —C(=O)N— group.

As used herein, an "alkoxy" or "alkoxy group" refers to an alkyl-O— group where "alkyl" is defined above.

As used herein, the term "aromatic" refers to a moiety having delocalized electrons due to conjugated double bonds, which may form a ring (as in an aryl moiety).

As used herein, the term "hydroxy" refers to a —OH group.

As used herein, the term "nitrile" or "nitrile group" refers to a —C≡N group.

As used herein, the term "halogen" or "halo" refers to fluoro, chloro, bromo, and iodo.

As used herein, "heteroaryl" or "heteroaryl group" refers to a monocyclic- or polycyclic aromatic ring comprising carbon atoms, hydrogen atoms, and one or more heteroatoms, preferably, 1 to 3 heteroatoms, independently selected from the group consisting of nitrogen, oxygen, and sulfur. The nitrogen group may be N, NH, or N-substituent, depending on the chosen ring and if substituents are recited. The nitrogen and sulfur heteroatoms may optionally be oxidized (e.g., S, S(O), S(O)$_2$, and N—O). The heteroaryl ring may be attached to its pendant group at any heteroatom or carbon atom that results in a stable structure. The heteroaryl rings described herein may be substituted on carbon or on a nitrogen atom if the resulting compound is stable. Examples of heteroaromatic groups include optionally substituted pyridyl, pyrrolyl, pyrimidinyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, 1,3,4-thiadiazolyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnnolinyl, napthyridinyl, pyridazinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl and benzoquinolyl.

As used herein, the term "polyether" refers to a group containing a plurality of ether groups.

As used herein, the term "substituted" refers to a radical in which one or more hydrogen atoms are each independently replaced with the same or different substituent(s). Examples of substituents include, but are not limited to, hydroxy, halogen, oxo, amino, carboxyl, alkoxy, carboxy, carboalkoxy, carboxamide, and nitrile.

As used herein, the term "flavor composition" refers to a composition that contains one or more compound(s) (e.g., co-ingredients) that provide(s) a desired taste when combined with a solvent that is suitable for oral administration and oral consumption. One of ordinary skill in the art of flavors is able to select them on the basis of its general knowledge and according to the nature of the product to be flavored and the desired taste.

As used herein, the term "consumer product" or "end product" refers to a composition that is in a form ready for use by the consumer for the marketed indication. A suitable solvent for use in a consumer product is a solvent that when combined with other components of the end product, will not render the consumer product unfit for its intended consumer use.

As used herein, the term "fragrance composition" refers to a mixture comprising one or more fragrance components, in any of their forms, and one or more solvents or perfuming co-ingredients. As known in the art, a fragrance composition will contain one or more fragrance components (e.g., perfuming co-ingredients) in order to impart an olfactory note to the composition (e.g., a household cleaner, perfume, or other commercial product) to which it is added.

In general terms, flavor and perfuming co-ingredients belong to chemical classes as varied as alcohols, aldehydes, ketones, esters, ethers, acetates, nitriles, terpene hydrocarbons, nitrogenous or sulphurous heterocyclic compounds and essential oils of natural or synthetic origin, and are well known to those of ordinary skill in the art. Many of these ingredients are listed in reference texts such as S. Arctander, *Perfume and Flavor Chemicals,* 1969, Montclair, N.J., USA or any of its more recent versions, each of which are hereby incorporated by reference.

The terms "Formula I", "Formula II" and "Formula III" include any sub-formulas.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

B. Compounds

The presently disclosed subject matter provides a compound of Formula I or a stereoisomer thereof,

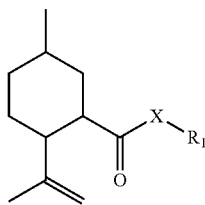

Formula I wherein X is O or N—$R_2$, and wherein $R_1$ and $R_2$ are selected from the group consisting of H, alkyl groups, alkenyl groups, aryl groups, and heteroaryl groups. In some embodiments, each of H, the alkyl groups, the alkenyl groups, the aryl groups, and the heteroaryl groups is substituted with at least one selected from the group consisting of hydroxy groups, alkoxy groups, carboxy groups, carboalkoxy groups, carboxamide groups, and nitrile groups. Examples of Formula I compound include, but are not limited to, N-ethyl-5-methyl-2-(prop-1-en-2-yl)cyclohexanecarboxamide, N-cyclopropyl-5-methyl-2-(prop-1-en-2-yl)cyclohexanecarboxamide, N-isopropyl-5-methyl-2-(prop-1-en-2-yl)cyclohexanecarboxamide, N-(tert-butyl)-5-methyl-2-(prop-1-en-2-yl)cyclohexanecarboxamide, N-(sec-butyl)-5-methyl-2-(prop-1-en-2-yl)cyclohexanecarboxamide, ethyl 2-(5-methyl-2-(prop-1-en-2-yl)cyclohexanecarboxamido)acetate, N-(4-methoxyphenyl)-5-methyl-2-(prop-1-en-2-yl)cyclohexanecarboxamide, or N-(4-(cyanomethyl)phenyl)-5-methyl-2-(prop-1-en-2-yl)cyclohexanecarboxamide. Preferably, the compound of Formula I is N-ethyl-5-methyl-2-(prop-1-en-2-yl)cyclohexanecarboxamide, or N-(4-(cyanomethyl)phenyl)-5-methyl-2-(prop-1-en-2-yl)cyclohexanecarboxamide.

Additionally, the presently disclosed subject matter provides a compound of Formula II or a stereoisomer thereof,

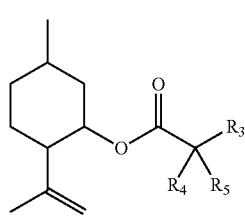

Formula II wherein $R_3$, $R_4$, and $R_5$ are selected from the group consisting of H, alkyl groups, alkenyl groups, aryl groups, and heteroaryl groups, and wherein $R_5$ is not H, a $C_1$-$C_{10}$ aliphatic group, or a $C_1$-$C_{10}$ aromatic group when both $R_3$ and $R_4$ are H. In some embodiments, each of H, the alkyl groups, the alkenyl groups, the aryl groups, and the heteroaryl groups is substituted with at least one selected from the group consisting of hydroxy groups, alkoxy groups, carboxy groups, carboalkoxy groups, carboxamide groups, and nitrile groups. Examples of Formula II compound include, but are not limited to, 4-((-5-methyl-2-(prop-1-en-2-yl)cyclohexyl)oxy)-4-oxobutanoic acid, 5-((-5-methyl-2-(prop-1-en-2-yl)cyclohexyl)oxy)-5-oxopentanoic acid, 5-methyl-2-(prop-1-en-2-yl)cyclohexyl 2-hydroxypropanoate, 5-methyl-2-(prop-1-en-2-yl)cyclohexyl 3-oxobutanoate, and 5-methyl-2-(prop-1-en-2-yl)cyclohexyl 3-hydroxybutanoate.

Furthermore, the presently disclosed subject matter provides a compound of Formula III or a stereoisomer thereof,

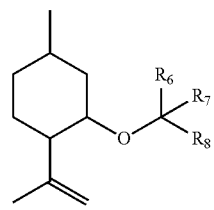

Formula III wherein $R_6$, $R_7$, and $R_8$ are selected from the group consisting of H, alkyl groups, alkenyl groups, aryl groups, and heteroaryl groups, and wherein $R_8$ is not a polyether when both $R_6$ and $R_7$ are H. In some embodiments, each of H, the alkyl groups, the alkenyl groups, the aryl groups, and the heteroaryl groups is substituted with at least one selected from the group consisting of hydroxy groups, alkoxy groups, carboxy groups, carboalkoxy groups, carboxamide groups, and nitrile groups. Examples of Formula III compound include, but are not limited to, 2-((5-methyl-2-(prop-1-en-2-yl)cyclohexyl)oxy)acetic acid, and N-isobutyl-2-((5-methyl-2-(prop-1-en-2-yl)cyclohexyl)oxy)acetamide.

The compounds of the presently disclosed subject matter have asymmetric centers, geometric centers (e.g., double bond), or both. All chiral, enantiomeric, diastereomeric, racemic forms and all geometric isomeric forms of a structure are intended. Compounds of the presently disclosed subject matter containing an asymmetrically substituted atom may be isolated in optically active or racemic forms. It is well known in the art how to prepare optically active forms, such as by resolution of racemic forms, by synthesis from optically active starting materials, through use of chiral auxiliaries, through asymmetric synthesis techniques, or through separation by crystallization or chromatographic means. Geometric isomers of olefins, C═N double bonds, or other types of double bonds may be present in the compounds described herein, and all such stable isomers are included in the present presently disclosed subject matter. Specifically, cis and trans geometric isomers of the compounds of the presently disclosed subject matter may also exist and may be isolated as a mixture of isomers or as separated isomeric forms. All processes used to prepare compounds of the presently disclosed subject matter and intermediates made therein are considered to be part of the presently disclosed subject matter. All tautomers of shown or described compounds are also considered to be part of the presently disclosed subject matter.

For example, compounds of Formula I can exist as any of the diastereomers as shown below.

I-1
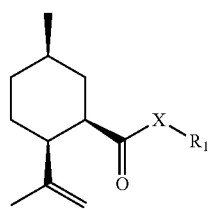
I-2
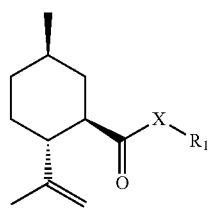
I-3
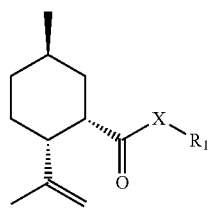
I-4
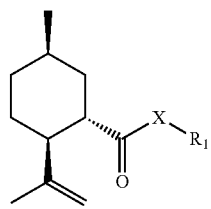
I-5
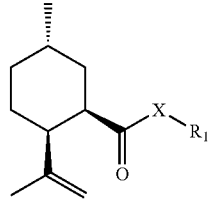
I-6
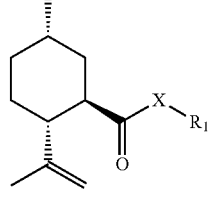
I-7
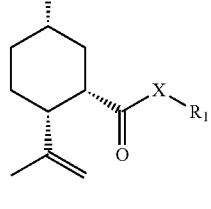
I-8
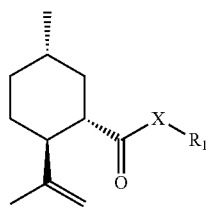
X and $R_1$ are defined as in Formula I above.
Compounds of Formula II can exist as any of the diastereomers as shown below.
II-1
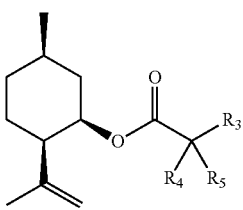
II-2
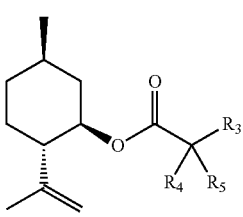
II-3
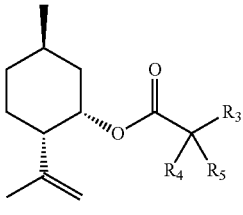
II-4
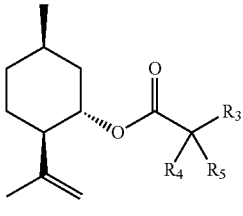
II-5
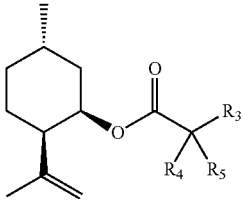

II-6

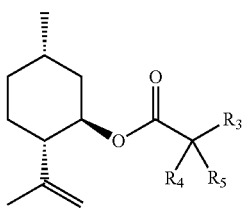

II-7

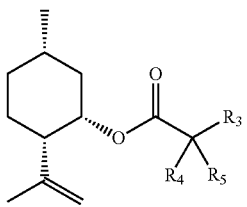

II-8

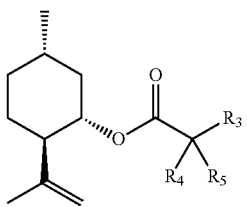

$R_3$, $R_4$ and $R_5$ are defined as in Formula II above.

Compounds of Formula III can exist as any of the diastereomers as shown below.

III-1

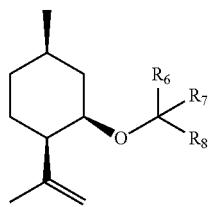

III-2

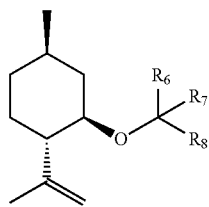

III-3

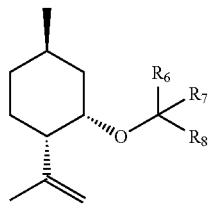

III-4

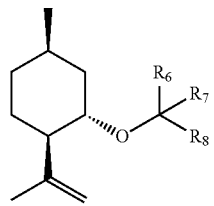

III-5

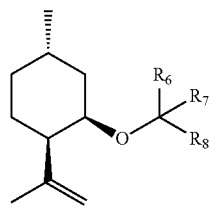

III-6

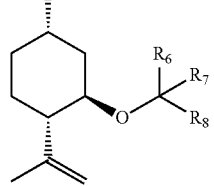

III-7

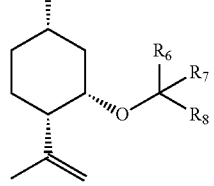

III-8

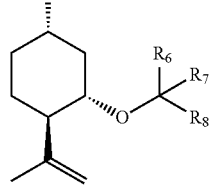

$R_6$, $R_7$ and $R_8$ are defined as in Formula III above.

1. Method of Preparation

The presently disclosed subject matter provides methods for preparing the compounds of Formulas I, II, and III, or stereoisomers thereof.

1.1 Preparation for Formula I Compounds

In one embodiment, isopulegol (I) is treated with an N-halosuccinimide and a trialkyl- or triaryl-phosphine to afford 2-chloro-4-methyl-1-isopropenylcyclohexane (II) as denoted in Scheme 1. Examples of N-halosuccinimide include, but are not limited to, N-chlorosuccinimide, N-bromosuccinimide, and N-iodosuccinimide. Preferably, N-halosuccinimide is N-chlorosuccinimide. Preferably, the trialkyl- or triaryl-phosphine is triphenylphosphine. The synthesis of 2-chloro-4-methyl-1-(prop-1-en-2-yl)cyclohexane from isopulegol is described in Dean and Whittaker *J. Chem. Soc. Perkin Trans.*, (1990):1275-1277. Isopulegol is widely available to one of ordinary skill in the art in the flavor and fragrance industry. A commercial grade of 1-isopulegol is available from Takasago International Corporation as Coolact® P.

Scheme 1

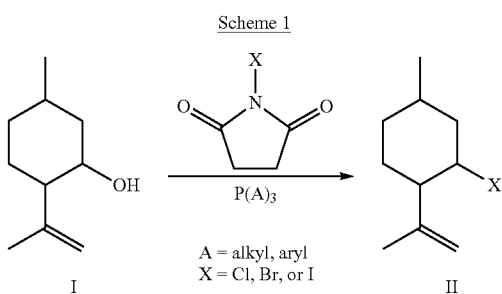

A = alkyl, aryl
X = Cl, Br, or I

The halo compound (II) is reacted with magnesium metal in a solvent to prepare the corresponding Grignard product (III) as denoted in Scheme 2. Suitable solvent includes, but is not limited to, tetrahydrofuran, dioxane, and diethylether. Preferably, the solvent is tetrahydrofuran. Subsequently, the Grignard product is quenched using a source of $CO_2$ to afford 5-methyl-2-isopropenylcyclohexanecarboxylic acid (IV) as denoted in Scheme 2.

Scheme 2

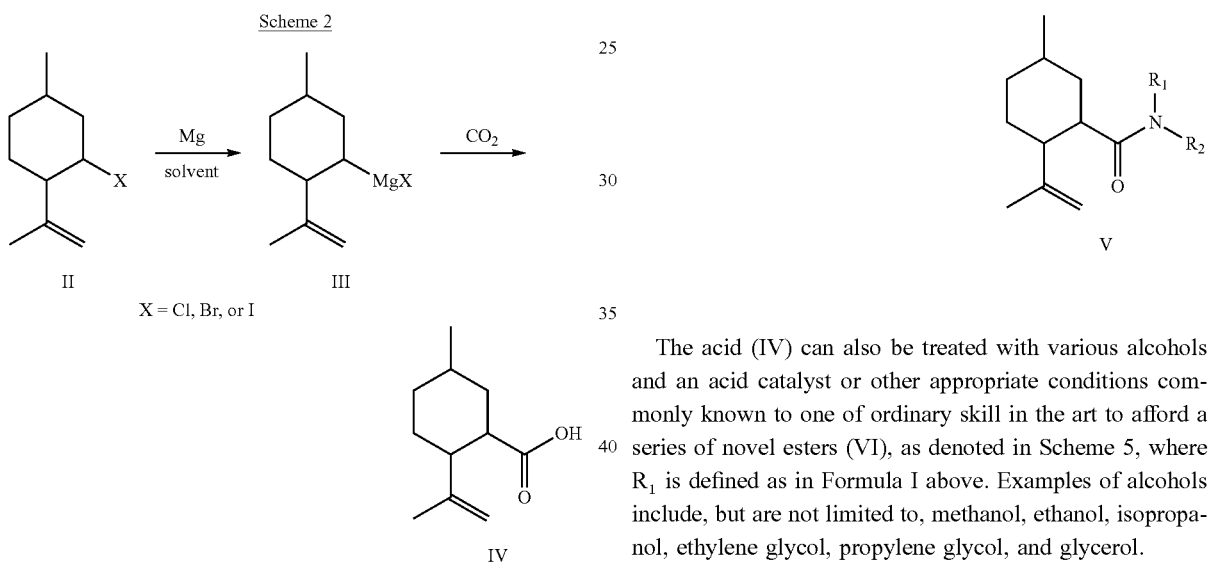

X = Cl, Br, or I

The acid (IV) can be coupled to various amines (NHR$_1$R$_2$) to afford a series of novel amides (V) as denoted in Scheme 3, wherein R$_1$ and R$_2$ are defined as in Formula I above. Examples of the coupling reagent include, but are not limited to 2-chloro-1-methylpyridinium iodide, N,N'-dicyclohexylcarbodiimide, and N,N'-diisopropylcarbodiimide.

Scheme 3

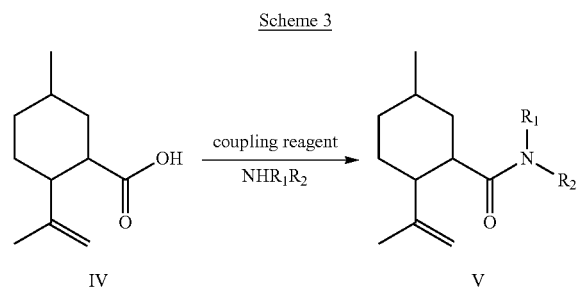

Alternatively, the acid (IV) can first be reacted with a chlorinating agent followed by the appropriate amine (NHR$_1$R$_2$) to afford the series of novel amides (V) as denoted in Scheme 4, wherein R$_1$ and R$_2$ are defined as in Formula I above. Examples of chlorinating agents include, but are not limited to, thionyl chloride and oxalyl chloride.

Scheme 4

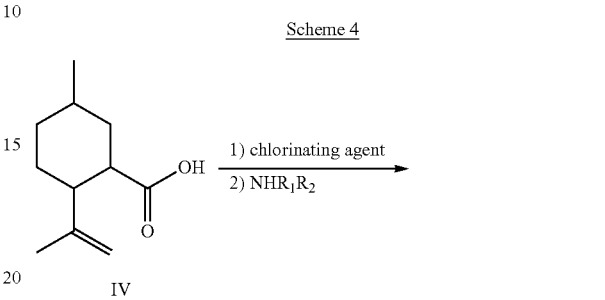

The acid (IV) can also be treated with various alcohols and an acid catalyst or other appropriate conditions commonly known to one of ordinary skill in the art to afford a series of novel esters (VI), as denoted in Scheme 5, where R$_1$ is defined as in Formula I above. Examples of alcohols include, but are not limited to, methanol, ethanol, isopropanol, ethylene glycol, propylene glycol, and glycerol.

Scheme 5

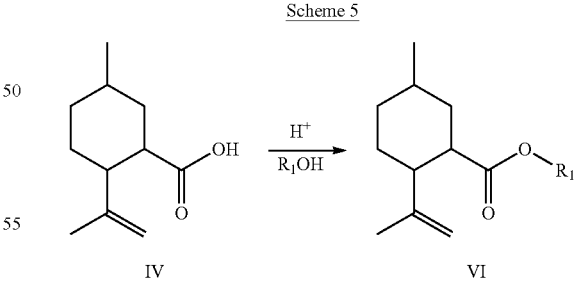

1.2 Preparation for Formula II Compounds

In one embodiment, isopulegol (I) is treated with various acid anhydrides at elevated temperature to afford a series of isopulegyl half-esters (VII), as denoted in Scheme 6. The elevated temperate can vary from 60° C. to 90° C.

Scheme 6

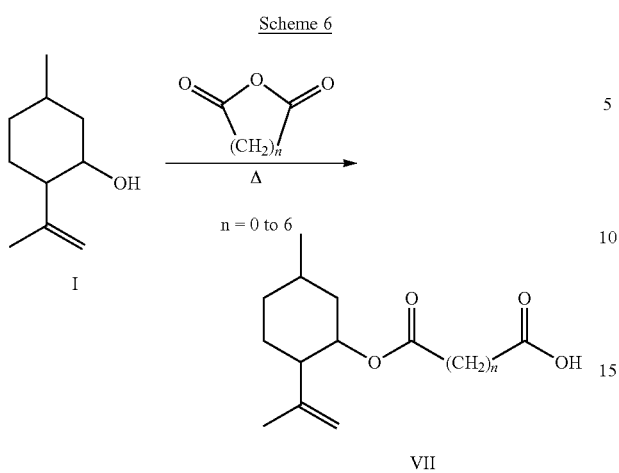

Alternatively and additionally, isopulegol (I) can be coupled directly with various organic acids or acid chlorides under appropriate conditions commonly known to one of ordinary skill in the art to afford a series of novel esters (VIII), as denoted in Scheme 7, wherein $R_3$, $R_4$, and $R_5$ are denoted in Formula II above. Examples of organic acids include, but are not limited to, priopionic acid, butyric acid, caproic acid, crotonic acid, oxalic acid, and malonic acid. Examples of acid chlorides include, but are not limited to, propionyl chloride, butyryl chloride, caproyl chloride, and crotonyl chloride.

Scheme 7

1.3 Preparation for Formula III Compounds

In one embodiment, isopulegol (I) is treated with an alkali metal or a strong base, and then reacted with a variety of alcohols ($R_6R_7R_8COH$) to afford a wide range of ethers (IX) as denoted in Scheme 8, wherein $R_6$, $R_7$, and $R_8$ are denoted in Formula III above. Examples of alkali metal include, but are not limited to, sodium and potassium. Examples of strong base include, but are not limited to, sodium hydride and potassium hydride. Examples of alcohols include, but are not limited to, ethanol, isopropanol, t-butanol, ethylene glycol, propylene glycol, and glycerol.

Scheme 8

2. Properties

The compounds of the presently disclosed subject matter impart a sensory effect to the skin of a subject, such as the oral and nasal cavity or topical areas, and possess flavor modulation properties. For example, the compounds of the presently disclosed subject matter impart cooling, warming, burning, tingling, numbing, salivating, musty, bitter, and/or astringent sensation. In addition, the compounds of the presently disclosed subject matter can impart tropical, fruity (e.g., berry), minty, phenolic, and vegetable (e.g., peppery) notes as well as creaminess and sweetness to flavor ingredients. The organoleptic properties of certain compounds of Formulas I, II, and III are described in Tables 1, 2, and 3, respectively.

TABLE 1

Formula I

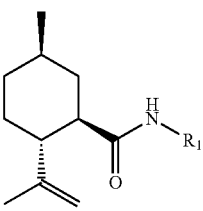

| Compound No. | $R_1$ | Name | Organoleptic Properties |
|---|---|---|---|
| 1 | —CH$_2$CH$_3$ | (1R,2R,5R)-N-ethyl-5-methyl-2-(prop-1-en-2-yl)cyclohexanecarboxamide | cooling, tingling, numbing |
| 2 |  | (1R,2R,5R)-N-cyclopropyl-5-methyl-2-(prop-1-en-2-yl)cyclohexanecarboxamide | slight cooling, salivating |
| 3 | —CH(CH3)$_2$ | (1R,2R,5R)-N-isopropyl-5-methyl-2-(prop-1-en-2-yl)cyclohexanecarboxamide | slight cooling |

TABLE 1-continued

Formula I

| Compound No. | R₁ | Name | Organoleptic Properties |
|---|---|---|---|
| 4 | —C(CH3)₃ | (1R,2R,5R)-N-(tert-butyl)-5-methyl-2-(prop-1-en-2-yl)cyclohexanecarboxamide | slight burn, warming, irritation |
| 5 | —CH(CH₃)CH₂CH₃ | (1,2R,5R)-N-(sec-butyl)-5-methyl-2-(prop-1-en-2-yl)cyclohexanecarboxamide | bitter, cooling |
| 6 | —CH₂CO₂CH₂CH₃ | (1R,2R,5R)-ethyl 2-(5-methyl-2-(prop-1-en-2-yl)cyclohexanecarboxamido)acetate | bitter, cooling, irritation |
| 7 | —C₆H₄—OMe | (1R,2R,5R)-N-(4-methoxyphenyl)-5-methyl-2-(prop-1-en-2-yl)cyclohexanecarboxamide | musty, astringent, slight cooling |
| 8 | —C₆H₄—CH₂CN | (1R,2R,5R)-N-(4-(cyanomethyl)phenyl)-5-methyl-2-(prop-1-en-2-yl)cyclohexanecarboxamide | phenolic, strong burning |

TABLE 2

Formula II

| Compound No. | R3 | R4 | R5 | Name | Organoleptic Properties |
|---|---|---|---|---|---|
| 9 | —CH₂CO₂H | —H | —H | (1R,2S,5R)-4-((-5-methyl-2-(prop-1-en-2-yl)cyclohexyl)oxy)-4-oxobutanoic acid | fruity, chemical, slight cooling/burn |
| 10 | —CH₂CH₂CO₂H | —H | —H | (1R,2S,5R)-5-((-5-methyl-2-(prop-1-en-2-yl)cyclohexyl)oxy)-5-oxopentanoic acid | sweet, fruity, slight cooling |
| 11 | —CH₃ | —OH | —H | (1R,2S,5R)-5-methyl-2-(prop-1-en-2-yl)cyclohexyl 2-hydroxypropanoate | minty, bitter, cooling |
| 12 | COCH₃ | —H | —H | (1R,2S,5R)-5-methyl-2-(prop-1-en-2-yl)cyclohexyl 3-oxobutanoate | bitter, fruity |
| 13 | C(OH)CH₃ | —H | —H | (1R,2S,5R)-5-methyl-2-(prop-1-en-2-yl)cyclohexyl 3-hydroxybutanoate | bitter, mild peppery |

TABLE 3

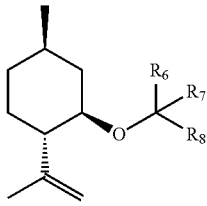

Formula II

| Compound | R6 | R7 | R8 | Name | Organoleptic Properties |
|---|---|---|---|---|---|
| 14 | —CO₂H | —H | —H | (1R,2S,5R)-2-((5-methyl-2-(prop-1-en-2-yl)cyclohexyl)oxy)acetic acid | fruity, creamy |
| 15 | —CONHCH₂CH(CH₃)₂ | —H | —H | (1R,2S,5R)-N-isobutyl-2-((5-methyl-2-(prop-1-en-2-yl)cyclohexyl)oxy)acetamide | bitter, tingle/burning |

The compounds of the presently disclosed subject matter show a surprising set of sensory attributes that are not found in current commercially available menthyl analogs. For example, (1R,2R,5R)—N-ethyl-5-methyl-2-(prop-1-en-2-yl)cyclohexanecarboxamide (Compound 1 as listed in Table 1) is shown to provide a cooling, tingling, and numbing sensation while its corresponding menthyl analog, N-ethyl-5-methyl-2-isopropylcyclohexanecarboxamide (as described in U.S. Pat. No. 4,150,052 and commonly known as WS-3), is generally known to provide a "clean cool" sensation. Additionally, it has been discovered that Compound 1 enhances the warming effect of pungent compounds much better than WS-3. See Example 20 for details. In addition, (1R,2R,5R)—N-(4-(cyanomethyl)phenyl)-5-methyl-2-(prop-1-en-2-yl)cyclohexanecarboxamide (Compound 8 as listed in Table 1) is shown to enhance and lengthen the cooling of a mouth-rinse composition better than WS-3. See Example 21 for details. Therefore, the attributes of the compounds of the presently disclosed subject matter provide for significant flavor modification and sensory experiences not available from current commercially available menthyl analogs.

C. Compositions

1. Flavor Compositions

The compounds of the presently disclosed subject matter can be employed, alone or in combination with other co-ingredients, in a flavor composition. The compounds of the presently disclosed subject matter can be used as physiological agents that impart positive sensory effects or modify the sensory properties of a wide variety of products in the flavor industry, including but not limited to, foodstuffs such as baked goods, cereals, dairy products, desserts; beverages such as juices, sodas, teas, flavored waters, fruit-based "smoothie" drinks, milk-based drinks; confectionaries such as sweets, pressed mints, hard candy, gums; and gelatinous materials, snacks, desserts, pharmaceutical and over-the-counter (OTC) products, oral care products and the like.

The compounds of the presently disclosed subject matter, in any of their forms, can be incorporated into flavoring compositions or flavored products, alone or in combination with co-ingredients or adjuvants, to impart taste to flavoring compositions, foods or beverages. Consequently, the use of the compounds of the presently disclosed subject matter, in any of their forms, as flavoring ingredients, is another object of the present invention, as is a flavor composition comprising a compound of the presently disclosed subject matter.

In one embodiment, the flavor composition of the presently disclosed subject matter comprising a compound of Formula I, including but not limited to, N-ethyl-5-methyl-2-(prop-1-en-2-yl)cyclohexanecarboxamide, N-cyclopropyl-5-methyl-2-(prop-1-en-2-yl)cyclohexanecarboxamide, N-isopropyl-5-methyl-2-(prop-1-en-2-yl)cyclohexanecarboxamide, N-(tert-butyl)-5-methyl-2-(prop-1-en-2-yl)cyclohexanecarboxamide, N-(sec-butyl)-5-methyl-2-(prop-1-en-2-yl)cyclohexanecarboxamide, ethyl 2-(5-methyl-2-(prop-1-en-2-yl)cyclohexanecarboxamido)acetate, N-(4-methoxyphenyl)-5-methyl-2-(prop-1-en-2-yl) cyclohexanecarboxamide, and N-(4-(cyanomethyl)phenyl)-5-methyl-2-(prop-1-en-2-yl)cyclohexanecarboxamide. In a specific embodiment, the flavor composition comprising N-ethyl-5-methyl-2-(prop-1-en-2-yl)cyclohexanecarboxamide. In another specific embodiment, the flavor composition comprising N-(4-(cyanomethyl)phenyl)-5-methyl-2-(prop-1-en-2-yl)cyclohexanecarboxamide.

In one embodiment, the flavor composition of the presently disclosed subject matter comprising a compound of Formula II, including but not limited to, 4-((−5-methyl-2-(prop-1-en-2-yl)cyclohexyl)oxy)-4-oxobutanoic acid, 5-((−5-methyl-2-(prop-1-en-2-yl)cyclohexyl)oxy)-5-oxopentanoic acid, 5-methyl-2-(prop-1-en-2-yl)cyclohexyl 2-hydroxypropanoate, 5-methyl-2-(prop-1-en-2-yl)cyclohexyl 3-oxobutanoate, and 5-methyl-2-(prop-1-en-2-yl)cyclohexyl 3-hydroxybutanoate.

In one embodiment, the flavor composition of the presently disclosed subject matter comprising a compound of Formula III, including but not limited to, 2-((5-methyl-2-(prop-1-en-2-yl)cyclohexyl)oxy)acetic acid, and N-isobutyl-2-((5-methyl-2-(prop-1-en-2-yl)cyclohexyl)oxy)acetamide.

The flavor compositions of the presently disclosed subject matter may be in the form of a simple mixture of flavoring ingredients or in an encapsulated form, e.g., a flavoring composition entrapped into a solid matrix that may comprise wall-forming and plasticizing materials such as mono-, di- or tri-saccharides, natural or modified starches, hydrocolloids, cellulose derivatives, polyvinyl acetates, polyvinylalcohols, proteins or pectins. Examples of particularly useful matrix materials include, but are not limited to, sucrose, glucose, lactose, levulose, fructose, maltose, ribose, dextrose, isomalt, sorbitol, mannitol, xylitol, lactitol, maltitol, pentatol, arabinose, pentose, xylose, galactose, maltodextrin, dextrin, chemically modified starch, hydrogenated starch hydrolysate, succinylated or hydrolysed starch, agar, carrageenan, gum arabic, gum accacia, tragacanth, alginates, methyl cellulose, carboxymethyl cellulose, hydroxyethyl cellulose, hydroxypropylmethyl cellulose, derivatives, gelatin, agar, alginate and mixtures thereof. Encapsulation is well-known to one of ordinary skill in the art, and may be performed, for example, using techniques such as spray-drying, agglomeration or extrusion, or coating encapsulation, including coacervation and complex coacervation techniques.

The compounds of the presently disclosed subject matter are valuable as being capable of imparting a sensory effect to the skin of a subject (e.g., the oral and nasal cavity), and possessing flavor modulation properties. For example, the compounds of the presently disclosed subject matter impart cooling, warming, burning, tingling, numbing, salivating, musty, bitter, and/or astringent sensation. See Tables 1-3. In addition, the compounds of the presently disclosed subject matter can impart tropical, fruity (e.g., berry), minty, phenolic, and vegetable (e.g., peppery) notes as well as creaminess and sweetness to flavor ingredients. See Tables 1-3. Specifically, the compounds of the presently disclosed subject matter show a surprising set of sensory attributes that are not found in current commercially available menthyl analogs. For example, as shown in Example 20, (1R,2R,5R)—N-ethyl-5-methyl-2-(prop-1-en-2-yl)cyclohexanecarboxamide (Compound 1 as listed in Table 1) enhances the warming effect of pungent compounds much better than N-ethyl-5-methyl-2-isopropylcyclohexanecarboxamide (WS-3). As shown in Example 21, (1R,2R,5R)—N-(4-(cyanomethyl)phenyl)-5-methyl-2-(prop-1-en-2-yl)cyclohexanecarboxamide (Compound 8 as listed in Table 1) enhances and lengthens the cooling of a mouth-rinse composition better than WS-3. Therefore, the attributes of the compounds of the presently disclosed subject matter provide for significant flavor modification and sensory experiences not available from current commercially available menthyl analogs.

The amounts of the compounds of the presently disclosed subject matter in a flavor composition vary depending on the nature of the flavor composition and can be determined by one of ordinary skill in the art. For example, the compound of the presently disclosed subject matter (e.g., a compound of Formula I, II, or III) is present in an amount of from about 0.0001% to about 99%, from about 0.0001% to about 75%, from about 0.001% to about 50%, from about 0.001% to about 35%, from about 0.001% to about 20%, from about 0.01% to about 20%, from about 0.01% to about 10%, from about 0.1% to about 5%, and from about 0.1% to about 1% weight by weight in a flavor composition. For example, N-ethyl-5-methyl-2-(prop-1-en-2-yl)cyclohexanecarboxamide, a compound of Formula I, enhances the warming perception in an amount of from about 0.1% to about 1% (e.g., about 0.5%) weight by weight in a hot and spicy flavor composition. See e.g., Example 17. In addition, N-(4-(cyanomethyl)phenyl)-5-methyl-2-(prop-1-en-2-yl)cyclohexanecarboxamide, a compound of Formula I, imparts an improved lingering burning sensation in an amount of from about 0.1% to about 1% (e.g., about 0.5%) weight by weight in a wasabi-type flavor composition. See e.g., Example 18. Additionally, 5-((−5-methyl-2-(prop-1-en-2-yl)cyclohexyl)oxy)-5-oxopentanoic acid, a compound of Formula II, imparts an extended cooling and increased astringency in an amount of from about 0.1% to about 1% (e.g., about 0.5%) weight by weight in a mouthwatering flavor composition. See e.g., Example 19. One of ordinary skill in the art is able to employ the desired amount of the compounds of the presently disclosed subject matter to provide the desired flavor and intensity. Much higher concentrations may be employed when the compounds are used in concentrated flavors and flavor compositions.

In certain embodiments, the flavor composition of the presently disclosed subject matter includes at least one sensation invoking material. The sensation invoking material can be a cooling ingredient, a warming ingredient, a tingling-type ingredient, or a combination thereof.

Examples of cooling ingredient include, but are not limited to, menthol, menthone, camphor, pulegol, isopulegol, cineole, 2-isopropyl-N,2,3-trimethylbutyramide, N-ethyl-2-isopropyl-5-methylcyclohexane carboxamide, ethyl 3-(p-menthane-3-carboxamido)acetate, N-(4-methoxyphenyl)-p-menthanecarboxamide, N-ethyl-2,2-diisopropylbutanamide, N-cyclopropyl-5-methyl-2-isopropylcyclohexanecarboxamide, N-(1,1-dimethyl-2-hydroxyethyl)-2,2-diethylbutanamide, N-(4-cyanomethylphenyl)-p-menthanecarboxamide, N-(2-(Pyridin-2-yl)ethyl)-3-p-menthanecarboxamide, N-(2-hydroxyethyl)-2-isopropyl-2,3-dimethylbutanamide, cyclopropanecarboxylic acid (2-isopropyl-5-methyl-cyclohexyl)-amide, N-[4-(2-Amino-2-oxoethyl)phenyl]-p-menthanecarboxamide, menthyl pyrrolidone carboxylate, cubebol, icilin, 2-isopropyl-5-methylcyclohexyl 4-(dimethylamino)-4-oxobutanoate, N-benzo[1,3]dioxol-5-yl-3-p-menthanecarboxamide, N-benzooxazol-4-yl-3-p-menthanecarboxamide, N-4-([1,2,4]triazol-1-yl)-phenyl-3-p-menthanecarboxamide & N-4-(pyrazol-1-yl)-phenyl-3-p-menthanecarboxamide, N-(1-isopropyl-1,2-dimethylpropyl)-1,3-benzodioxole-5-carboxamide, N-(1-methyl-1-isopropylbutyl)benzamide, fenchyl-N,N-diemethylsuccinamide, fenchyl monosuccinate, ethyl fenchyl malonate, bornyl monosuccinate, isobornyl monosuccinate, menthyl 3-oxobutyrate, menthyl 3-oxopentanoate, 3-1-menthoxypropane-1,2-diol, 3-1-menthoxy-2-methylpropane-1,2-diol, p-menthane-3,8-diol, 2-1-menthoxyethan-1-ol, 3-1-menthoxypropan-1-ol, 4-1-menthoxybutan-1-ol, menthyl 3-hydroxybutanate, 6-isopropyl-9-methyl-1,4-dioxaspiro-(4,5)-decane-2-methanol, 2-[(2-p-menthoxy)ethoxy]ethanol, menthyl succinate, menthyl glutarate, dimenthyl succinate, dimenthyl glutarate, menthyl lactate, menthol glycerin ketal, mint oil, peppermint oil, spearmint oil, eucalyptus oil, and all mixtures, salts, and stereoisomers thereof.

Examples of warming ingredient include, but are not limited to, vanillyl ethyl ether, vanillyl propyl ether, vanillin propylene glycol acetal, ethyl vanillin propylene glycol acetal, capsaicin, gingerol, vanillyl butyl ether, 4-(1-menthoxy-methyl)-2-phenyl-1,3-dioxolane, 4-(1-menthoxy-methyl)-2-(3',4'-dihydroxy-phenyl)-1,3-dioxolane, 4-(1-menthoxy-methyl)-2-(2'-hydroxy-3'-methoxy-phenyl)-1,3-dioxolane, 4-(1-menthoxy-methyl)-2-(4'-methoxyphenyl)-1,3-dioxolane, 4-(1-menthoxy-methyl)-2-(3'4'-methylenedioxy-phenyl)-1,3-dioxolane, hot pepper oil, capsicum oleoresin, ginger oleoresin, nonyl acid vanillylamide, 4-(1-menthoxy-methyl)-2-(3'-methoxy-4'-hydroxy-phenyl)-1,3-dioxolane, vanillin-1,2-hexylene glycol acetal, vanillin-1,2-butylene glycol acetal, vanillin-1-butoxyglycerol acetal, and all mixtures and stereoisomers thereof.

Examples of tingling-type ingredient include, but are not limited to, spilanthol, sanshool, hydroxy α-sanshool, hydroxy-sanshool, hydroxy γ-sanshool, sanshool-I, sanshool II, sanshoamide, Japanese pepper extract, black pepper extract, chavicine, piperine, echinacea extract, northern prickly ash extract, Nepalese spice timur extract, red pepper oleoresin, 4-(1-menthoxymethyl)-2-phenyl-1,3-dioxolane, N-isobutyldeca-(2,4)-dienamide, N-cyclopropyl-(2E,6Z)-nonadienamide, N-ethyl-(2E,6Z)-nonadienamide, jambu oleoresin, and all mixtures and stereoisomers thereof.

The compounds of the presently disclosed subject matter can be incorporated alone or in or on a support material including, but not limited to, solvents, oils, sugars, or resins, into a flavor composition. Examples of solvents commonly used in a flavor composition are well known in the art, including but not limited to, propylene glycol, triacetin, triethyl citrate, benzyl alcohol, benzyl benzoate, ethanol, vegetable oils and terpenes.

In certain embodiments, the compounds of the presently disclosed subject matter are incorporated or included in chewing and bubble gums and confectionaries (e.g., hard or soft candies or lozenges). Chewing gum compositions typically include one or more gum bases and other standard components such as flavoring agents, softeners, sweeteners and the like. Flavoring agents for use in chewing gum compositions are well known in the art and include natural flavors such as citrus oils, peppermint oil, spearmint oil, oil of wintergreen, natural menthol, cinnamon, ginger and the like; artificial flavors such as menthol, carvone, limonene, cinnamic aldehyde, linalool, geraniol, ethyl butyrate, and the like. As well known in the art, the ingredients used in chewing gum compositions can include sweeteners that can be natural or artificial, and can be sugar or sugarless. Sweeteners are typically present in the chewing gum compositions in amounts of from about 20% to about 80% by weight, preferably from about 30% to about 60% by weight, based on the total weight of the chewing gum composition. Sugarless sweeteners include, but are not limited to, sugar alcohols such as Sorbitol, manifold, xylitol, hydrogenated starch hydrolysates, malitol and the like. High intensity sweeteners such as Sucralose®, Aspartame®, Neotame®, salts of acesulfame, and the like, when employed, are typically present up to about 1.0% by weight.

In certain embodiments, the compounds of the presently disclosed subject matter are incorporated or included in an oral personal care product (e.g., a mouthwash or toothpaste). For example, a mouthwash can be prepared by dissolving a flavor composition (e.g., a flavor cocktail; liquid or powder) that includes a compound of the presently disclosed subject matter in a solvent (e.g., water) that further includes, for example, a flavor such as menthol and a surfactant; and then mixing the resulting solution with, for example, an aqueous erythritol solution.

In certain embodiments, the compounds of the presently disclosed subject matter are added, directly or indirectly, to a pharmaceutical dosage form (e.g., a tablet, capsule, drop or lozenge) that contains a therapeutically active agent (e.g., a medicament). For example, the presently disclosed subject matter provides a cough drop or lozenge comprising one or more compounds of the presently disclosed subject matter and, optionally, further comprising menthol or other medicaments for treating sore throat, coughing or other upper respiratory ailments.

In certain embodiments, the compounds of the presently disclosed subject matter are added to, for example, compositions for the preparation of: 1) carbonated or non-carbonated fruit beverages, carbonated cola drinks, wine coolers, fruit liquors, cordials, milk drinks, "smoothy" drinks, flavored water, tropical alcoholic and "virgin" drink mixes (e.g., margarita, piña colada or "rum-runner" concentrates), and powders for drinks (e.g., powdered sports or "hydrating" drinks); 2) frozen confectioneries such as ice creams, sherbets, and ice-lollies, hard candies, soft candies, taffies, chocolates, and sugarless candies; 3) desserts such as jelly and pudding; 4) confectioneries such as cakes, cookies, chewing gums and bubble gums; 5) condiments, spices and seasonings, dry cereals, oatmeals, and granola bars; 6) alcoholic beverages, energy beverages, juices, teas, coffees, salsa, and gel beads; 7) film strips for halitosis, and oral personal care products; 8) gelatin candies, pectin candies, starch candies, lozenges, cough drops, throat lozenges, throat sprays, and toothpastes.

In certain embodiments, the compounds of the presently disclosed subject matter are added to, for example; 1) Japanese confectioneries such as buns with bean-jam filling, bars of sweet jellied bean paste, and sweet jellied pounded rice; 2) jams; candies; 3) breads; 4) beverages such as green tea, oolong tea, black tea, persimmon leaftea, Chamomile tea, Sasa veitchii tea, mulberry leaf tea, Houttuynia cordata tea, Puer tea, Mate tea, Rooibos tea, Gimunema tea, Guava tea, coffee, espresso, and hot and cold espresso and coffee products obtained by mixing espresso and/or coffee with milk, water or other liquids suitable for oral consumption (e.g., lattes, cafe au lait, cafe mocha) and cocoa; 5) soups such as Japanese flavor soup, western flavor soup, and Chinese flavor soup; 6) seasonings; 7) various instant beverages and foods; 8) various snack foods; and 9) other compositions for oral use.

In certain embodiments, the use level of the compound of the presently disclosed subject matter in an end product ranges of from about 0.1 ppm to about 10,000 ppm, and from about δ ppm to about 2,500 ppm, by weight based on the total weight of the end product.

2. Fragrance Compositions

The compounds of the presently disclosed subject matter can be incorporated into fragrance compositions, including but not limited to, candles; air fresheners; perfumes; colognes; personal care products such as soaps, deodorants, shampoos, conditioners, shower gels and shaving lotions; cosmetics such as lotions and ointments; as well as detergents; fabric care products and household cleaner/cleaning agents. More specifically, the compounds of the presently disclosed subject matter can be added to, for example: 1) fragrance products, perfume, eau de perfume, eau de toilet, eau de cologne, and the like, skin-care cosmetics, face washing creams, varnishing creams, cleansing creams, cold creams, massage creams and oils, milky lotions, skin toning lotion, cosmetic solutions, packs, makeup remover, and the like; 2) makeup cosmetics, foundations, face powders, pressed powders, talcum powders, lip sticks, lip creams, cheek powders, eyeliners, mascara, eye shadows, eyebrow pencils, eye packs, nail enamels, nail enamel removers, and the like; 3) hair care cosmetics, pomades, brilliantines, setting lotions, hair sticks, hair solids, hair oils, hair treatments, hair creams, hair tonies, hair liquids, hair sprays, hair restorers, hair dyes, and the like; 4) sunburn cosmetics, suntan products, sunscreen products, and the like; 5) medical cosmetics, antiperspirants, after-shave lotions and gels, permanent wave lotions, medicated soaps, medicated shampoos, medicated skin care products, and the like; 6) hair care products, shampoos, rinses, shampoo-including-rinses, hair conditioners, hair treatments, hair packs, and the like; 7) as soaps, toilet soaps, bath soaps, perfumed soaps, transparent soaps, synthetic soaps, and the like; 8) body washing soaps, body soaps, body shampoos, hand soaps, and the like; 9) bathing, bathing agents (e.g., bath salts, bath tablets, bath liquids, and the like), foam baths (bubble bath and the like), bath oils (e.g., bath perfumes, bath capsules and the like), milk baths, bath gels, bath cubes, and the like; 10) detergents, heavy duty detergents for clothes, light duty detergents for clothes, liquid detergents, laundering soaps, compact detergents, powder soaps, and the like; 11) softening finishing agents, softeners, furniture care products, and the like; and deodorants, aromatic substances and the like; 12) insect repellent, insecticides, and the like; 13) oral care products such as tooth pastes, mouth cleaners, mouth wash, troches, chewing gums, and the like; and 14) pharmaceutical and OTC products, poultices, external skin care pharmaceuticals such as ointments, internal administration medicines, and the like.

EXAMPLES

The following examples are merely illustrative of the presently disclosed subject matter and they should not be considered as limiting the scope of the presently disclosed subject matter in any way.

The present application is further described by means of the examples presented below, wherein the abbreviations have the usual meaning in the art. The melting points (m.p) and boiling points (b.p.) listed are uncorrected and all temperatures are indicated in degrees Centigrade (° C.). Melting point is defined as the temperature at which a solid turns into a liquid, and is obtained at standard atmospheric pressure using a Fisher-Johns melting point apparatus. Boiling point is defined as the temperature at which a liquid turns to vapor at the designated pressure, and is obtained by vacuum distillation. The nuclear magnetic resonance (NMR) spectral data were recorded in chloroform-d ($CDCl_3$), unless otherwise stated, using a 400 MHz instrument (manufactured by JEOL) for both proton ($^1H$) and carbon ($^{13}C$) spectroscopy. The chemical shifts (δ) listed are indicated in ppm with respect to tetramethylsilane as reference. The relative area under a peak in a $^1H$ experiment corresponds to the number of hydrogen atoms associated with the individual functional group. Multiplicity associated with each peak is indicated as singlet (s), broad singlet (bs), doublet (d), triplet (t), quartet (q), doublet of doublets (dd), and multiplet (m).

Example 1—Preparation of (1R,2R,5R)-5-methyl-2-(prop-1-en-2-yl)cyclohexanecarboxylic acid 7.0 g (0.29 mol) of magnesium metal was added to 500 ml of anhydrous tetrahydrofuran and heated to 60° C. while stirring under a nitrogen atmosphere. 50.0 g (0.29 mol) of 2-chloro-4-methyl-1-(prop-1-en-2-yl)cyclohexane (prepared from 1-isopulegol using the procedure described in Dean and Whittaker *J. Chem. Soc. Perkin Trans.*, 1990, 1275-1277) was dissolved in 200 ml of anhydrous tetrahydrofuran and was added drop-wise to the stirred suspension at a rate to maintain a gentle reflux. When the addition was complete, the mixture was allowed to stir for an additional 16 h. $CO_2$ gas was then bubbled into the solution through a gas diffusor for 6 hours or until the reaction was complete. The solution was then quenched by drop-wise addition of 300 ml of 1N HCl. The resulting two phase mixture was transferred to a separatory funnel and the aqueous layer was removed. The organic layer was then washed consecutively with an additional 300 ml of 1N HCl, 300 ml of water, and 300 ml of saturated salt solution. The organic layer was then dried over anhydrous magnesium sulfate and the solvent was removed on a rotary evaporator to afford 48.2 g of a yellow oil. This yellow oil was then distilled to afford 43.6 g (83% yield) of a colorless oil which solidified to a waxy white solid upon standing.

m.p. −59-61° C.
$^1H$ NMR ($CDCl_3$): δ ppm 0.91 (d, 3H) 1.02 (m, 1H) 1.22 (m, 2H) 1.41 (tdd, 1H) 1.69 (m, 1H) 1.70 (s, 3H) 1.77 (m, 2H) 1.97 (m, 2H) 2.16 (td, 1H) 2.44 (td, 1H) 4.71 (s, 2H) 9.47 (bs, 1H).
$^{13}C$ NMR ($CDCl_3$): δ ppm 20.1, 22.2, 31.4, 31.7, 34.5, 38.0, 47.2, 47.6, 110.7, 147.7, 181.5.

Example 2—Preparation of (1R,2R,5R)—N-ethyl-5-methyl-2-(prop-1-en-2-yl)cyclohexanecarboxamide (Compound 1 in Table 1)

5.0 g (0.027 mol) of (1R,2R,5R)-5-methyl-2-(prop-1-en-2-yl)cyclohexanecarboxylic acid and 7.7 g (0.030 mol) of 2-chloro-1-methylpyridinium iodide are suspended in 50 ml of dichloromethane. To this was added drop-wise a solution of 15 ml of 2.0M ethylamine in hexane and 3.05 g (0.030 mol) of triethylamine in 25 ml of dichloromethane. This mixture was stirred at room temperature for 18 h. The resultant yellow slurry was then quenched with 50 ml of 1N HCl. This two-phase mixture was placed in a separatory funnel and the aqueous layer was removed. The organic layer was washed with 100 ml of 1M NaOH, 100 ml of water, and 100 ml of saturated salt solution. The organic layer was then dried over anhydrous magnesium sulfate and the solvent was removed on a rotary evaporator to afford 4.2 g of a pale yellow solid. The crude solid was recrystallized from 3:1 acetone/water to afford 3.1 g (54% yield) of a white solid.

m.p. −83-84° C.
$^1H$ NMR ($CDCl_3$): δ ppm 0.89 (d, 3H) 1.00 (m, 1H) 1.07 (t, 3H) 1.24 (m, 2H) 1.41 (m, 1H) 1.63 (m, 1H) 1.67 (s, 3H) 1.85 (m, 2H) 2.12 (m, 2H) 3.23 (m, 2H) 4.70 (s, 2H) 5.30 (bs, 1H).
$^{13}C$ NMR ($CDCl_3$): δ ppm 14.9, 20.5, 22.3, 31.8, 32.0, 34.0, 34.5, 38.7, 47.4, 49.9, 110.6, 148.2, 174.9.

Example 3—Preparation of (1R,2R,5R)—N-cyclopropyl-5-methyl-2-(prop-1-en-2-yl)cyclohexanecarboxamide (Compound 2 in Table 1)

According to the procedure from Example 2, using 1.7 g (0.030 mol) of cyclopropylamine, (1R,2R,5R)—N-cyclopropyl-5-methyl-2-(prop-1-en-2-yl)cyclohexanecarboxamide was obtained and was recrystallized from 2:1 acetone/water to afford 1.9 g (32% yield) of a white solid.

m.p. −118-119° C.
$^1H$ NMR ($CDCl_3$): δ ppm 0.40 (m, 2H) 0.72 (m, 2H) 0.90 (m, 3H) 1.01 (m, 1H) 1.30 (m, 4H) 1.69 (m, 5H) 1.80 (d, 2H) 2.09 (m, 2H) 2.61 (m, 1H) 4.70 (m, 2H) 5.50 (bs, 1H).
$^{13}C$ NMR ($CDCl_3$): δ ppm 6.6, 6.7, 20.5, 22.2, 22.3, 31.8, 32.0, 34.5, 38.5, 47.4, 49.4, 110.7, 148.2, 176.4.

Example 4—Preparation of (1R,2R,5R)—N-isopropyl-5-methyl-2-(prop-1-en-2-yl)cyclohexanecarboxamide (Compound 3 in Table 1)

According to the procedure from Example 2, using 1.8 g (0.030 mol) of iso-propylamine, (1R,2R,5R)—N-isopropyl-5-methyl-2-(prop-1-en-2-yl)cyclohexanecarboxamide was obtained and was recrystallized from 2:1 acetone/water to afford 2.8 g (46% yield) of a white solid.

m.p. −96-98° C.
$^1H$ NMR ($CDCl_3$): δ ppm 0.88 (d, 3H) 0.97 (m, 1H) 1.05 (d, 6H) 1.26 (m, 1H) 1.37 (m, 1H) 1.76 (m, 5H) 2.03 (m, 2H) 2.13 (m, 2H) 4.00 (m, 1H) 4.71 (s, 2H) 5.19 (bs, 1H).
$^{13}C$ NMR ($CDCl_3$): δ ppm 20.4, 22.3, 22.7, 22.9, 31.8, 32.0, 34.6, 38.6, 41.3, 47.5, 49.8, 110.7, 148.2, 174.0.

Example 5—Preparation of (1R,2R,5R)—N-(tert-butyl)-5-methyl-2-(prop-1-en-2-yl)cyclohexanecarboxamide (Compound 4 in Table 1)

According to the procedure from Example 2, using 2.2 g (0.030 mol) of tert-butylamine, (1R,2R,5R)—N-(tert-butyl)-5-methyl-2-(prop-1-en-2-yl)cyclohexanecarboxamide was obtained and was recrystallized from 75% ethanol to afford 3.6 g (56% yield) of a white solid.

m.p −146-148° C.
$^1H$ NMR ($CDCl_3$): δ ppm 0.88 (d, 3H) 0.93 (m, 1H) 1.00 (m, 1H) 1.25 (m, 9H) 1.38 (m, 2H) 1.70 (m, 5H) 1.80 (m, 1H) 1.96 (m, 1H) 2.11 (m, 1H) 4.72 (s, 2H) 5.16 (bs, 1H).
$^{13}C$ NMR ($CDCl_3$): δ ppm 20.4, 22.3, 28.8, 31.9, 32.0, 34.6, 38.6, 47.6, 50.3, 50.8, 110.7, 148.3, 174.3.

Example 6—Preparation of (1R,2R,5R)—N-(sec-butyl)-5-methyl-2-(prop-1-en-2-yl)cyclohexanecarboxamide (Compound 5 in Table 1)

According to the procedure from Example 2, using 2.2 g (0.030 mol) of sec-butylamine, (1R,2R,5R)—N-(sec-butyl)-5-methyl-2-(prop-1-en-2-yl)cyclohexanecarboxamide was obtained and was recrystallized from 2:1 acetone/water to afford 2.4 g (38% yield) of a white solid.
m.p −129-132° C.
$^1$H NMR (CDCl$_3$): δ ppm 0.84 (m, 3H) 0.89 (d, 3H) 1.02 (m, 4H) 1.25 (m, 2H) 1.39 (m, 3H) 1.71 (m, 5H) 1.83 (m, 1H) 2.12 (m, 2H) 3.85 (m, 1H) 4.71 (m, 2H) 5.16 (br. s., 1H).
$^{13}$C NMR (CDCl$_3$): δ ppm 10.1, 10.3, 20.4, 20.5, 20.6, 22.3, 29.7, 32.1, 34.6, 38.8, 46.0, 47.4, 49.8, 148.2, 174.2.

Example 7—Preparation of (1R,2R,5R)-ethyl 2-(5-methyl-2-(prop-1-en-2-yl)cyclohexanecarboxamido)acetate (Compound 6 in Table 1)

According to the procedure from Example 2, using 3.1 g (0.030 mol) of glycine ethyl ester, (1R,2R,5R)-ethyl 2-(5-methyl-2-(prop-1-en-2-yl)cyclohexanecarboxamido)acetate was obtained and was recrystallized from 2:1 ethanol/water to afford 3.1 g (43% yield) of a white solid.
m.p −78-81° C.
$^1$H NMR (CDCl$_3$): δ ppm 0.90 (d, 3H) 1.00 (m, 1H) 1.25 (m, 5H) 1.42 (m, 1H) 1.67 (s, 3H) 1.78 (m, 2H) 1.88 (m, 1H) 2.21 (m, 2H) 3.96 (dq, 2H) 4.18 (m, 2H) 4.70 (s, 2H) 5.92 (bs, 1H).
$^{13}$C NMR (CDCl$_3$): δ ppm 14.1, 20.4, 22.2, 31.8, 32.0, 34.5, 38.7, 41.2, 47.2, 49.4, 61.4, 110.7, 148.1, 170.1, 175.1.

Example 8—Preparation of (1R,2R,5R)—N-(4-methoxyphenyl)-5-methyl-2-(prop-1-en-2-yl)cyclohexanecarboxamide (Compound 7 in Table 1)

According to the procedure from Example 2, using 3.7 g (0.030 mol) of 4-methoxyaniline, (1R,2R,5R)—N-(4-methoxyphenyl)-5-methyl-2-(prop-1-en-2-yl)cyclohexanecarboxamide was obtained and was recrystallized from ethanol to afford 4.3 g (55% yield) of an off-white solid.
m.p −157-158° C.
$^1$H NMR (CDCl$_3$): δ ppm 0.91 (d, 3H) 1.05 (m, 1H) 1.30 (m, 2H) 1.45 (m, 1H) 1.76 (m, 5H) 1.95 (d, 1H) 2.25 (m, 2H) 3.76 (s, 3H) 4.77 (d, 2H) 6.81 (m, 2H) 7.05 (bs, 1H) 7.24 (m, 2H) 7.33 (m, 2H).
$^{13}$C NMR (CDCl$_3$): δ ppm 20.8, 22.3, 31.9, 32.0, 34.5, 38.7, 47.4, 50.6, 55.5, 110.9, 114.1, 121.9, 131.6, 148.4, 156.2, 173.1.

Example 9—Preparation of (1R,2R,5R)—N-(4-(cyanomethyl)phenyl)-5-methyl-2-(prop-1-en-2-yl)cyclohexanecarboxamide (Compound 8 in Table 1)

According to the procedure from example 2, using 3.6 g (0.030 mol) of 4-aminophenylacetonitrile, (1R,2R,5R)—N-(4-(cyanomethyl)phenyl)-5-methyl-2-(prop-1-en-2-yl)cyclohexanecarboxamide was obtained and was recrystallized from heptane to afford 2.7 g (34% yield) of a pale yellow solid.
m.p −106-107° C.
$^1$H NMR (CDCl$_3$): δ ppm 0.93 (d, 3H) 1.02 (m, 1H) 1.31 (m, 2H) 1.47 (m, 1H) 1.75 (m, 5H) 1.96 (m, 1H) 2.28 (m, 2H) 3.68 (s, 2H) 4.78 (s, 2H) 7.18 (bs, 1H) 7.22 (m, 2H) 7.46 (m, 2H).
$^{13}$C NMR (CDCl$_3$): δ ppm 20.4, 21.8, 23.1, 28.0, 32.3, 34.1, 38.0, 45.5, 47.4, 51.5, 110.9, 112.0, 118.1, 120.4, 128.4, 138.3, 148.7, 173.6.

Example 10—Preparation of (1R,2S,5R)-4-((−5-methyl-2-(prop-1-en-2-yl)cyclohexyl)oxy)-4-oxobutanoic acid (Compound 9 in Table 2)

10.0 g (0.065 mol) of isopulegol and 8.7 g (0.097 mol) of succinic anhydride were stirred together under a nitrogen blanket at 90° C. for 18 hours. The crude product was then distilled to remove any unreacted starting material and then fractionally distilled to afford 7.8 g (47% yield) of (1R,2S,5R)-4-((−5-methyl-2-(prop-1-en-2-yl)cyclohexyl)oxy)-4-oxobutanoic acid as a colorless oil.
b.p. −105-111° C. (0.6 mm)
$^1$H NMR (CDCl$_3$): δ ppm 0.91 (d, 3H) 1.02 (m, 2H) 1.33 (m, 1H) 1.52 (m, 1H) 1.62 (s, 3H) 1.67 (m, 2H) 1.97 (m, 1H) 2.09 (m, 1H) 2.51 (m, 2H) 2.66 (m, 2H) 4.69 (d, 2H) 4.78 (m, 1H) 10.24 (bs, 1H).
$^{13}$C NMR (CDCl$_3$): δ ppm 19.3, 22.0, 29.0, 29.1, 30.3, 31.3, 34.0, 40.3, 50.7, 74.0, 111.8, 146.0, 171.4, 178.4.

Example 11—Preparation of (1R,2S,5R)-5-((−5-methyl-2-(prop-1-en-2-yl)cyclohexyl)oxy)-5-oxopentanoic acid (Compound 10 in Table 2)

According to the procedure from Example 10, using 11.0 g (0.097 mol) of glutaric anhydride, 10.1 g (58% yield) of (1R,2S,5R)-5-((−5-methyl-2-(prop-1-en-2-yl)cyclohexyl)oxy)-5-oxopentanoic acid was obtained as a colorless oil.
b.p −110-114° C. (0.5 mm)
$^1$H NMR (CDCl$_3$): δ ppm 0.90 (d, 3H) 0.98 (m, 2H) 1.34 (m, 1H) 1.52 (m, 1H) 1.63 (s, 3H) 1.68 (m, 2H) 1.88 (m, 1H) 1.95 (m, 1H) 2.08 (m, 1H) 2.30 (m, 2H) 2.37 (m, 2H) 4.70 (d, 2H) 4.79 (m, 1H) 10.55 (bs, 1H).
$^{13}$C NMR (CDCl$_3$): δ ppm 19.4, 19.8, 22.0, 30.3, 31.3, 32.9, 33.5, 34.0, 40.4, 50.7, 73.7, 111.8, 146.1, 172.3, 179.2.

Example 12—Preparation of (1R,2S,5R)-5-methyl-2-(prop-1-en-2-yl)cyclohexyl 2-hydroxypropanoate (Compound 11 in Table 2)

10.0 g (0.065 mol) of isopulegol, 10.0 g (0.112 mol) of L-lactic acid, and 0.25 g (0.001 mol) of p-toluenesulfonic acid were dissolved in 20 ml of heptane in a round bottom flask equipped with a Dean-Stark trap. The solution was heated to reflux and the resulting water generated was collected in the trap. After refluxing for 6 hours the reaction was allowed to cool to room temperature and the resulting solution was stirred with 50 ml of 50% aqueous sodium hydroxide solution for 2 hours. The organic layer was dried over anhydrous magnesium sulfate and concentrated on a rotary evaporator. The crude product was then distilled to afford 7.1 g (48% yield) of (1R,2S,5R)-5-methyl-2-(prop-1-en-2-yl)cyclohexyl 2-hydroxypropanoate as a pale yellow oil.
b.p −117-122° C. (1 mm)
$^1$H NMR (CDCl$_3$): δ ppm 0.92 (3H, d) 1.25 (1H, m) 1.33 (1H, m) 1.45 (3H, d) 1.53 (1H, m) 1.58 (4H, m) 1.63 (1H, m) 1.94 (1H, m) 2.22 (1H, m) 4.38 (1H, q) 4.97 (1H, d) 4.98 (1H, d) 5.12 (1H, m).

Example 13—Preparation of (1R,2S,5R)-5-methyl-2-(prop-1-en-2-yl)cyclohexyl 3-oxobutanoate (Compound 12 in Table 2)

10.0 g (0.065 mol) of isopulegol, 11.3 g (0.097 mol) of methyl acetoacetate, and 0.2 g (0.001 mol) of p-toluenesulfonic acid were dissolved in 25 ml of heptane in a round bottom flask equipped with a Dean-Stark trap. The solution was heated to reflux and the resulting water generated was collected in the trap. After refluxing for 6 hours the reaction was allowed to cool to room temperature and the solvent was removed on a rotary evaporator. The crude product was then distilled to afford 11.6 g (75% yield) of (1R,2S,5R)-5-methyl-2-(prop-1-en-2-yl)cyclohexyl 3-oxobutanoate as a colorless oil.

b.p −118-125° C. (1 mm)

$^1$H NMR (CDCl$_3$): δ ppm 0.92 (3H, d) 1.25 (1H, m) 1.33 (1H, m) 1.53 (1H, m) 1.58 (4H, m) 1.62 (2H, m) 1.94 (1H, m) 2.12 (3H, s) 2.22 (1H, m) 3.56 (2H, s) 4.97 (2H, s) 5.11 (1H, m).

Example 14—Preparation of (1R,2S,5R)-5-methyl-2-(prop-1-en-2-yl)cyclohexyl 3-hydroxybutanoate (Compound 13 in Table 2)

5 g (0.021 mol) of (1R,2S,5R)-5-methyl-2-(prop-1-en-2-yl)cyclohexyl 3-oxobutanoate (as obtained in Example 13) was dissolved in 20 ml of tetrahydrofuran and this solution was cooled to −20° C. To this cooled mixture was added a solution of 0.2 g (0.005 mol) of sodium borohydride in 20 ml of tetrahydrofuran drop-wise at a rate to keep the reaction temperature below 0° C. at all times. After the addition was complete, reaction was stirred at 0° C. for 1 hour and then was allowed to warm to room temperature and stirred overnight. The reaction was quenched with 25 ml of 1N HCl and the organic layer was washed with 50 ml of water. The organic phase was dried over anhydrous magnesium sulfate, concentrated on a rotary evaporator, and the crude product was then purified by silica gel column chromatography using 5% ethyl acetate in hexane as eluent to afford 0.5 g (10% yield) of (1R,2S,5R)-5-methyl-2-(prop-1-en-2-yl)cyclohexyl 3-hydroxybutanoate as a colorless oil.

$^1$H NMR (CDCl$_3$): δ ppm 0.92 (3H, d) 1.17 (3H, d) 1.25 (1H, m), 1.33 (1H, m) 1.53 (1H, m) 1.57 (4H, m) 1.61 (1H, m), 1.65 (1H, m) 1.94 (1H, m) 2.22 (1H, m) 2.48 (2H, d) 3.95 (1H, m), 4.98 (2H, s) 5.11 (1H, m).

Example 15—Preparation of (1R,2S,5R)-2-((5-methyl-2-(prop-1-en-2-yl)cyclohexyl)oxy)acetic acid (Compound 14 in Table 3)

In a 500 ml round bottom flask was suspended 8.1 g (0.337 mol) of sodium hydride (60% dispersion in mineral oil) in 250 ml of anhydrous xylenes under a nitrogen atmosphere. The suspension was heated to reflux and 20.0 g (0.130 mol) of isopulegol was added drop-wise over a period of 4 hours. To the resulting mixture was added a solution of 14.7 g (0.156 mol) of chloroacetic acid in 50 ml of anhydrous xylenes over 90 minutes and the mixture stirred for an additional 2 hours. After allowing the solution to cool to room temperature, the reaction was quenched by drop-wise addition of cold 10% HCl solution. The organic layer was washed twice with 250 ml of water, dried over anhydrous magnesium sulfate, and then concentrated and diluted with 100 ml of toluene. To the resulting toluene solution was added a solution of 25 ml of 28% sodium methoxide in methanol followed by 80 ml of water. The aqueous layer was washed twice with 100 ml of toluene and then acidified by adding 35% HCl to pH 3. The resulting organic layer was distilled to give 14.3 g (52% yield) of (1R,2S,5R)-2-((5-methyl-2-(prop-1-en-2-yl)cyclohexyl)oxy)acetic acid as a pale yellow oil.

b.p −100-102° C. (0.5 mm)

$^1$H NMR (CDCl$_3$): δ ppm 0.92 (3H, d) 1.24 (1H, m) 1.33 (1H, m) 1.55 (5H, m) 1.60 (1H, m) 1.66 (1H, m) 1.82 (1H, m), 2.16 (1H, m) 3.50 (1H, m), 4.08 (2H, s) 4.97 (2H, s) 9.63 (1H, bs).

Example 16—Preparation of (1R,2S,5R)—N-isobutyl-2-((5-methyl-2-(prop-1-en-2-yl)cyclohexyl)oxy) acetamide (Compound 15 in Table 3)

2.6 g (0.012 mol) of (1R,2S,5R)-2-((5-methyl-2-(prop-1-en-2-yl)cyclohexyl)oxy)acetic acid (as prepared in Example 15) and 3.1 g (0.012 mol) of 2-chloro-1-methylpyridinium iodide are suspended in 25 ml of dichloromethane. To this was added drop-wise a solution of 0.88 g (0.012 mol) of iso-butylamine and 2.43 g (0.024 mol) of triethylamine in 25 ml of dichloromethane. This mixture was stirred at room temperature for 18 h. The workup was completed as described in Example 2. The resulting crude product was purified by silica gel column chromatography using 5% ethyl acetate in hexane as eluent to afford 0.47 g (15% yield) of (1R,2S,5R)—N-isobutyl-2-((5-methyl-2-(prop-1-en-2-yl)cyclohexyl)oxy)acetamide as a colorless oil.

$^1$H NMR (CDCl$_3$): δ ppm 0.85 (6H, d) 0.92 (3H, d) 1.24 (1H, m), 1.43 (1H, m) 1.58 (5H, m) 1.69 (1H, m) 1.78 (2H, m) 1.81 (1H, m) 2.19 (1H, m) 3.19 (2H, d), 3.46 (1H, m), 3.95 (2H, s), 4.98 (2H, s) 5.04 (1H, bs).

Example 17—A Warming Flavor Composition Comprising (1R,2R,5R)—N-ethyl-5-methyl-2-(prop-1-en-2-yl)cyclohexanecarboxamide (Compound 1 in Table 1)

Compound 1 was tested in the following hot and spicy flavor composition Formula A and tasted by eight trained evaluators in water at 0.05% (2.5 ppm dosage of Compound 1), compared to a control Formula B that does not contain Compound 1 as shown below.

|  | Formula A | Formula B |
|---|---|---|
| Capsicum oleoresin, nat. (w/w %) | 2.0 | 2.0 |
| Cinnamon bark oil, nat. (w/w %) | 0.2 | 0.2 |
| Cinnamic aldehyde, nat. (w/w %) | 0.1 | 0.1 |
| Ethyl alcohol, 95%, nat. (w/w %) | 97.2 | 97.7 |
| Compound 1 (w/w %) | 0.5 | — |

Each evaluator was asked to rate the warming level in the mouth on a scale of 1-9 over a 5 minute period after swishing & spitting the sample. Compound 1 was found to enhance the initial heat perception in Formula A and evaluators reported a stronger overall burning sensation with more intense heat than the control Formula B as shown in the table below.

| Time (min) | Rated warming Level for Formula A | Rated warming Level for Formula B |
|---|---|---|
| 0.5 | 5.0 | 4.4 |
| 1 | 5.1 | 4.2 |
| 5 | 2.8 | 2.7 |

Example 18—A Wasabi-Type Flavor Composition Comprising (1R,2R,5R)—N-(4-(cyanomethyl)phenyl)-5-methyl-2-(prop-1-en-2-yl)cyclohexanecarboxamide (Compound 8 in Table 1)

Compound 8 was tested in the following wasabi-type flavor composition Formula C and tasted by eight trained evaluators in water at 0.2% (10 ppm dosage of Compound 8) compared to a control Formula D that does not contain Compound 8 as shown below.

|  | Formula C | Formula D |
| --- | --- | --- |
| Mustard oil, nat (w/w %) | 1.0 | 1.0 |
| Ethyl alcohol, 95%, nat. (w/w %) | 98.5 | 99.0 |
| Compound 8 (w/w %) | 0.5 | — |

Formula C was selected as being preferred by 7 out of the 8 evaluators. The addition of Compound 8 added a more intense and lingering burning sensation and gave a more natural character to the wasabi-type flavor composition Formula C than the control Formula D.

Example 19—A Mouthwatering Composition Comprising (1R,2S,5R)-5-((5-methyl-2-(prop-1-en-2-yl)cyclohexyl)oxy)-5-oxopentanoic acid (Compound 10 in Table 2)

Compound 10 was tested in the following mouthwatering composition Formula E and tasted by three expertly trained evaluators in water at 0.05% (2.5 ppm dosage of Compound 10) compared to a control Formula F that does not contain Compound 10 as shown below.

|  | Formula E | Formula F |
| --- | --- | --- |
| Jambu oleoresin (30% in PG) (w/w %) | 2.0 | 2.0 |
| Menthol, nat. (w/w %) | 0.05 | 0.05 |
| Vanillin (w/w %) | 0.1 | 0.1 |
| Propylene glycol (w/w %) | 97.35 | 97.85 |
| Compound 10 (w/w %) | 0.5 | — |

All three expert evaluators felt that Formula E had a more pleasant mouthwatering effect with extended cooling and increased astringency. Formula E was preferred by all three evaluators over Formula F.

Example 20—Comparison of the Warming Enhancement Properties of (1R,2R,5R)—N-ethyl-5-methyl-2-(prop-1-en-2-yl)cyclohexanecarboxamide (Compound 1 in Table 1) with its Corresponding Menthyl Analog, N-ethyl-5-methyl-2-isopropylcyclohexanecarboxamide (WS-3)

Compound 1 was tested for its synergistic enhancement of the warming effect from pungent compound vanillyl butyl ether (VBE). A stock solution of 1% VBE in ethanol was prepared. This stock solution was then added at 0.2% in water to produce a 20 ppm tasting solution (Control). To subsequent 20 ppm tasting solutions was added 2.5 ppm of Compound 1 (Formula G) and 2.5 ppm WS-3 (Formula H). Ten trained evaluators were asked to rate heat intensity in the mouth and rank the three samples for preference after swishing and spitting the sample.

Formula G was selected as being preferred by seven out of the ten evaluators over both Control and Formula H. Panelists described Formula G as comprising a quick onset and clean heat which was much more pleasant than either the Control or Formula H.

Example 21—Comparison of the Cooling Enhancement Properties of (1R,2R,5R)—N-(4-(cyanomethyl)phenyl)-5-methyl-2-(prop-1-en-2-yl)cyclohexanecarboxamide (Compound No. 8 in Table 1) Against N-ethyl-5-methyl-2-isopropylcyclohexanecarboxamide (WS-3) in a Mouth-Rinse Composition Compound 8 was tested in the following mouth-rinse composition Formula J and evaluated over a 20 minute period by five expertly trained evaluators, compared to two other mint flavor compositions, a Control and Formula K that contains WS-3 as shown below.

|  | Control | Formula J | Formula K |
| --- | --- | --- | --- |
| Mint flavor (w/w %) | 80 | 75 | 75 |
| Menthol, nat. (w/w %) | 20 | 20 | 20 |
| Compound 8 (w/w %) | — | 5 | — |
| WS-3 (w/w %) | — | — | 5 |

The compositions were each dissolved at 0.1% in the following mouth-rinse base (50 ppm dosage of Compound 8 & WS-3 respectively).

| Sodium lauryl sulfate, 30% in water | 1% |
| --- | --- |
| Sorbitol | 2% |
| Sodium Saccharin | 0.05% |
| Sodium Benzoate | 0.08% |
| Menthol, nat. | 0.02% |
| Glycerin, nat., 99.7% | 7% |
| Water | 89.85% |

The evaluators were asked to rate cooling intensity on a scale of 1-9 in the mouth at 0, 0.5, 1, 5, 10, and 20 minutes. It was found that Formula J enhanced and lengthened the cooling perception of the mouth-rinse composition after 1 minute over both the Control and Formula K as shown in the table below.

| Time (min) | Rated cooling intensity for Control | Rated cooling intensity for Formula J | Rated cooling intensity for Formula K |
| --- | --- | --- | --- |
| 0 | 4.3 | 4.0 | 4.3 |
| 0.5 | 5.1 | 4.3 | 4.4 |
| 1 | 4.8 | 4.8 | 4.8 |
| 5 | 2.8 | 3.8 | 3.4 |
| 10 | 2.0 | 2.8 | 2.1 |
| 20 | 1.3 | 1.6 | 1.3 |

The present presently disclosed subject matter is not to be limited in scope by the specific embodiments described herein. Indeed, various modifications of the presently disclosed subject matter in addition to those described herein will become apparent to those skilled in the art from the foregoing description and the accompanying figures. Such modifications are intended to fall within the scope of the appended claims.

Patents, patent applications publications product descriptions, and protocols are cited throughout this application the disclosures of which are incorporated herein by reference in their entireties for all purposes.

What is claimed is:

1. A compound of Formula I or a stereoisomer thereof,

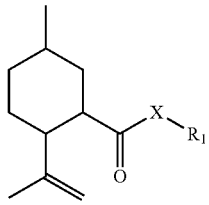

Formula I wherein X N—R₂, and wherein R₁ and R₂ are selected from the group consisting of H, alkyl groups, alkenyl groups, aryl groups, and heteroaryl groups.

2. The compound of claim 1, wherein the compound is selected from the group consisting of N-ethyl-5-methyl-2-(prop-1-en-2-yl)cyclohexanecarboxamide, N-cyclopropyl-5-methyl-2-(prop-1-en-2-yl)cyclohexanecarboxamide, N-isopropyl-5-methyl-2-(prop-1-en-2-yl)cyclohexanecarboxamide, N-(tert-butyl)-5-methyl-2-(prop-1-en-2-yl)cyclohexanecarboxamide, N-(sec-butyl)-5-methyl-2-(prop-1-en-2-yl)cyclohexanecarboxamide, ethyl 2-(5-methyl-2-(prop-1-en-2-yl)cyclohexanecarboxamido)acetate, N-(4-methoxyphenyl)-5-methyl-2-(prop-1-en-2-yl) cyclohexanecarboxamide, and N-(4-(cyanomethyl)phenyl)-5-methyl-2-(prop-1-en-2-yl)cyclohexanecarboxamide.

3. The compound of claim 1, wherein the compound is N-ethyl-5-methyl-2-(prop-1-en-2-yl)cyclohexanecarboxamide.

4. The compound of claim 1, wherein the compound is N-(4-(cyanomethyl)phenyl)-5-methyl-2-(prop-1-en-2-yl) cyclohexanecarboxamide.

5. A flavor composition comprising from about 0.0001% to about 99% weight by weight of the compound of claim 1.

6. The flavor composition of claim 5, wherein the compound is present in an amount from about 0.001% to about 50% weight by weight in the flavor composition.

7. The flavor composition of claim 5, wherein the compound is present in an amount from about 0.01% to about 20% weight by weight in the flavor composition.

8. The flavor composition of claim 5, further comprising at least one sensation invoking material.

9. The flavor composition of claim 8, wherein the at least one sensation invoking material is selected from the group consisting of a warming ingredient, a cooling ingredient, a tingling ingredient, and a combination thereof.

10. A flavor composition comprising from about 0.0001% to about 99% weight by weight of a compound of Formula I or a stereoisomer thereof,

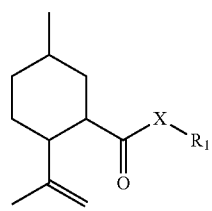

Formula I wherein X is O, and wherein R₁ is selected from the group consisting of H, alkyl groups, alkenyl groups, aryl groups, and heteroaryl groups.

11. The flavor composition of claim 10, wherein the compound is present in an amount from about 0.001% to about 50% weight by weight in the flavor composition.

12. The flavor composition of claim 10, wherein the compound is present in an amount from about 0.01% to about 20% weight by weight in the flavor composition.

13. The flavor composition of claim 10, further comprising at least one sensation invoking material.

14. The flavor composition of claim 13, wherein the at least one sensation invoking material is selected from the group consisting of a warming ingredient, a cooling ingredient, a tingling ingredient, and a combination thereof.

* * * * *